(12) United States Patent
Sorensen et al.

(10) Patent No.: US 6,500,108 B1
(45) Date of Patent: Dec. 31, 2002

(54) RADIATION DELIVERY SYSTEM AND METHOD

(75) Inventors: Scott A. Sorensen, Overland Park, KS (US); Thomas W. Robison, Los Alamos, NM (US); Craig M. V. Taylor, Jemez Springs, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/693,527

(22) Filed: Oct. 20, 2000

Related U.S. Application Data

(60) Provisional application No. 60/161,095, filed on Oct. 22, 1999.

(51) Int. Cl.[7] ............................................. A61N 5/00
(52) U.S. Cl. .................... 600/3; 424/1.11; 424/1.53
(58) Field of Search ......................... 600/1–8; 424/1.11, 424/1.53; 534/10

(56) References Cited

U.S. PATENT DOCUMENTS

| | | | |
|---|---|---|---|
| 5,683,345 A | 11/1997 | Waksman et al. | 600/3 |
| 5,707,332 A | 1/1998 | Weinberger | 600/3 |
| 5,730,698 A | 3/1998 | Fischell et al. | 600/3 |
| 5,871,436 A | 2/1999 | Eury | 600/3 |
| 5,891,956 A | 4/1999 | Smith et al. | 525/56 |
| 5,899,882 A | 5/1999 | Waksman et al. | 604/96 |
| 5,942,209 A | 8/1999 | Leavitt et al. | 424/1.25 |
| 6,077,213 A | 6/2000 | Ciezki et al. | 600/3 |
| 6,103,295 A | 8/2000 | Chan et al. | 427/5 |
| 6,106,454 A | 8/2000 | Berg et al. | 600/3 |
| 6,117,065 A | 9/2000 | Hastings et al. | 600/3 |

FOREIGN PATENT DOCUMENTS

| | | | |
|---|---|---|---|
| WO | WO9901179 | 1/1999 | 600/3 |

OTHER PUBLICATIONS

Colin D. Bain and George M. Whitesides, "Molecular–Level Control Over Surface Order in Self–Assembled Monolayer Films of Thiols on Gold," Science, vol. 240, pp. 62–63, Apr. 1988.

Murali Sastry, Vijaya Patil, and K.S. Mayya, "Selective Binding of Divalent Cations at the Surface of Self–Assembled Monolayers of an Aromatic Bifunctional Molecule Studied on a Quartz Crystal Microbalance," J. Phys. Chem. B. 1997, 101, 1167–1170.

Simon Flink, Frank C. J. M. van Veggel, and David N. Reinhoudt, "Recognition of Cations by Self–Assembled Monolayers of Crown Ethers," J. Phys. Chem. B. 1999, 103, 6515–6520.

Roger Alberto, Roger Schibli, and August P. Schubiger, "First Application of fac–$[^{99m}Tc(OH_2)_3(CO)_3]^+$ Fl in Bioorganometallic Chemistry: Design, Structure, and in Vitro Affinity of a $50HT_{1A}$ Receptor Ligand Labeled with $^{99m}Tc$," J. Am. Chem Soc. 1999, 121, 6076–6077.

Roger Alberto, Roger Schibli, Andre Egli, and August P. Schubiger, "A Novel Organometallic Aqua Complex of Technetium for the Labeling of Biomolecules: Synthesis of $[^{99m}Tc(OH_2)_3(CO)_3]$ from $[^{99m}TcO_4]^-$ in Aqueous Solution and Its Reaction with a Bifunctional Ligand," J. Am Chem. Soc. 1998, 120, 7987–7988.

Ralph G. Nuzzo and David L. Allara, "Adsorption of Bifunctional Organic Disulfides on Gold Surfaces," J. Am. Chem. Soc. 1983, 105, 4481–4483.

Urs O. Hafeli, Matthew C. Warburton, and Uziel Landau, "Eletrodeposition of Radioactive Rhenium onto Stents to Prevent Restenosis," Biomaterials 19, 1998, 925–933.

*Primary Examiner*—Max Hindenburg
(74) *Attorney, Agent, or Firm*—Samuel L. Borkowsky

(57) ABSTRACT

A radiation delivery system and method are described. The system includes a treatment configuration such as a stent, balloon catheter, wire, ribbon, or the like, a portion of which is covered with a gold layer. Chemisorbed to the gold layer is a radiation-emitting self-assembled monolayer or a radiation-emitting polymer. The radiation delivery system is compatible with medical catheter-based technologies to provide a therapeutic dose of radiation to a lesion following an angioplasty procedure.

15 Claims, 4 Drawing Sheets

RADIATION DELIVERY SYSTEM AND METHOD

RELATED APPLICATIONS

This application claims the benefit of provisional patent application No. 60/161,095 filed Oct. 22, 1999, which is hereby incorporated by reference.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to radiation delivery systems and more particularly, to a radiation delivery system and method for using the same for brachytherapy of benign, such as neointimal hyperplasia in coronary arteries (restenosis), or malignant proliferative disease.

BACKGROUND OF THE INVENTION

Restenosis is the recurrence of blood flow obstruction in blood vessels previously treated by percutaneous transluminal coronary angioplasty (PTCA), a medical procedure that improves vascularization of occluded blood vessels using a number of techniques that include catheter-based balloon expansion, stent placement, rotational artherectomy, laser ablation, etc. Although the exact mechanism that results in the production of restenosis is unclear, it is believed to involve neointimal or adventitia hyperplasia (i.e., cell proliferation), vascular recoil, inflammatory processes, or some combination thereof initiated by PTCA. Restenosis is reported to occur in 30 to 50 percent of all PTCA procedures, and follow-up treatment results in increased patient risks, complications, and health care costs (see Tilkian, A. G., and Daily, E. K. Cardiovascular Procedures. Diagnostic Techniques and Therapeutic Procedures. C. V. Mosby Company, St. Louis, Mo. 1986, ISBN 0-8016-4965-X, hereby incorporated by reference).

Intravascular brachytherapy (IVB), a medical procedure involving the delivery of a therapeutic dose of radiation to a tissue portion subsequent to PTCA treatment, shows great promise in reducing the rate of subsequent restenosis.

Typically, a radiation delivery system (RDS) is used for IVB that includes a PTCA catheter-based device such as a stent, balloon catheter, ribbon, wire, etc. that has been modified to include an attached radioactive material. (see Alice K. Jacobs in "Selection of Guiding Catheters, Practical Angioplasty, David Faxon ed., Raven Press, New York, 1993, hereby incorporated by reference). FIG. 1 shows a process flow chart describing the IVB process. Briefly, the RDS is used it irradiate a lesion following an angioplasty procedure. The RDS is inserted into the guiding catheter and into the body, and passes through the same blood vessels as during the angioplasty procedure. The RDS is positioned near the lesion and allowed to remain there until the radioactive element can provide a therapeutic radiation dose across the lesion.

Results from clinical trials indicate that IVB treatment of blood vessels with a radiation dose of about 15–30 Gray (Gy; 1 Gy=100 rads) significantly reduces the rate of restenosis after PTCA. Table 1 describes several radiation delivery systems that can be used for IVB.

TABLE 1

Radiation Delivery Systems for Intravascular Brachytherapy

| RDS | Radionuclide and method of production | Advantages | Disadvantages |
|---|---|---|---|
| Gamma wire | $^{192}$Ir neutron activation | Uniform dose distribution Small RDS diameters can pass through narrow vessels Re-usable | Offsite production of $^{192}$Ir Long Treatment times Radiation hazard to staff ($^{192}$Ir is a high energy γ source) |
| Beta wire | $^{90}$Y neutron activation | Minimal radiation hazard to staff (90Y is a high energy beta-emitter Re-usable | Offsite production of $^{90}$Y Long treatment times Weekly delivery |
| Beta source train | $^{90}$Sr/$^{90}$Y fission product | Minimal radiation hazard to staff since $^{90}$Y is a beta-emitter Re-usable | Offsite production Large RDS diameters limit use with small vessels |
| Coated stent and/or balloon | $^{32}$P fission product | stent can be left in place Minimal radiation hazard to staff | Offsite production β energy may be too low Frequent source exchanges |
| Liquid-filled balloon | $^{186}$Re or $^{188}$Re neutron activation $^{188}$W generator | High Energy β-emitter $^{188}$Re is available readily from a tungsten generator | Contamination hazard Radiation hazard to staff Frequent source exchanges |
| Gas-filled balloon | $^{133}$Xe fission product | $^{133}$Xe is a commonly used radionuclide | β energy of $^{133}$Xe may be too low Special ventilation required for radioactive gas |

Examples of the coated stent and/or balloon, and the liquid filled balloon, are described in U.S. Pat. No. 5,730,698 to R. E. Fischell entitled "Balloon Expandable Temporary Radioisotope Stent System", which issued Mar. 24, 1998. The '698 patent describes an over-the-wire balloon angioplasty catheter having a balloon surrounded by a reversibly deployable stent system. The balloon can be filled with a radioactive liquid, or the balloon and/or stent can be embedded or implanted with a radioactive material, such as $^{32}$P.

Some delivery systems, like the one described in the '698 patent, involve the insertion and removal of the RDS, while others include a detachable portion, such as a detachable stent, which remains in the body and continues to irradiate tissue after the rest of the device has been removed.

Radiation delivery systems are generally not manufactured at the treatment center, i.e. the hospital, clinic, or the like. This is unfortunate since the most desirable radionuclides cannot be used because they have relatively short half lives (hours) and would decay significantly during shipping. Radiation delivery systems are, therefore, limited to radionuclides with intermediate to long half-lives of days, weeks, or even longer.

Longer lived radionuclides have lower specific activities (SA), and present additional problems with RDS storage, handling and waste disposal. Some beta emitting and gamma emitting radionuclides and their specific activities are listed in Table 2.

TABLE 2

Specific Activities of Radionuclides

| Beta Emitter | SA (Ci/g) | Gamma Emitter | SA (Ci/g) |
|---|---|---|---|
| $^{32}$P | $2.88 \times 10^5$ | $^{57}$Co | $8.54 \times 10^3$ |
| $^{89}$Sr | $2.81 \times 10^4$ | $^{67}$Ga | $6.04 \times 10^5$ |
| $^{90}$Sr | $1.45 \times 10^2$ | $^{99m}$Tc | $5.33 \times 10^6$ |
| $^{90}$Y | $5.50 \times 10^5$ | $^{103}$Pd | $6.74 \times 10^4$ |
| $^{91}$Y | $2.47 \times 10^4$ | $^{109}$Cd | $2.62 \times 10^3$ |
| $^{131}$I | $1.25 \times 10^5$ | $^{111}$In | $4.24 \times 10^5$ |
| $^{133}$Xe | $1.89 \times 10^5$ | $^{123}$I | $1.93 \times 10^6$ |
| $^{170}$Tm | $5.79 \times 10^3$ | $^{125}$I | $1.75 \times 10^4$ |
| $^{186}$Re | $1.92 \times 10^5$ | $^{131}$Cs | $1.04 \times 10^5$ |
| $^{188}$Re | $9.97 \times 10^6$ | $^{145}$Sm | $2.68 \times 10^3$ |
| $^{204}$Tl | $4.6 \times 10^2$ | $^{153}$Gd | $3.56 \times 10^3$ |
| $^{210}$Bi | $1.25 \times 10^5$ | $^{169}$Yb | $2.46 \times 10^4$ |
| | | $^{192}$Ir | $9.29 \times 10^3$ |
| | | $^{197}$Hg | $2.51 \times 10^5$ |
| | | $^{201}$Tl | $2.16 \times 10^5$ |

There are clear advantages to a RDS that could be produced at or near the treatment center with short lived, high SA radionuclides. Short-lived radionuclides would allow administering the therapeutic dose over a short period of time, minimizing hazards to the patient, hospital workers, and anyone else handling the RDS. In addition, the clinician could select the treatment configuration of the RDS (balloon catheter, stent, guidewire, etc.) and the type of radiation (beta and or gamma radiation) at the treatment center and prepare the RDS immediately prior to use. The RDS geometry could then be based on actual patient parameters, such as the exact length of the lesion and vessel diameter, rather than the manufacturer predetermined parameters necessitated by offsite production.

Therefore, an object of the invention is a radiation delivery system that can deliver an effective dose of radiation to a tissue.

Another object of the invention is a radiation delivery system that can pass through narrow blood vessels.

Another object of the invention is a radiation delivery system that can be uniquely prescribed for a given patient and then manufactured and used at the treatment center.

Another object of the invention is a radiation delivery system that employs short-lived radionuclides with a high specific activity.

Yet another object of the invention is a radiation delivery system that remains intact after delivering a radiation dose to a tissue.

Still another object of the invention is a radiation delivery system that can be used for benign, such as neointimal hyperplasia in coronary arteries (restenosis), and malignant proliferative disease.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes a radiation delivery system that includes a treatment configuration, such as a stent, balloon, ribbon, wire, or the like. The treatment configuration has a surface, at least a portion of which is coated with a layer of gold metal. One embodiment of the invention includes a radiation-emitting self assembled monolayer that is chemisorbed to the gold layer. Another embodiment of the invention includes a radiation-emitting polymer that is chemisorbed to the gold layer.

The invention also includes a method for preparing a radiation delivery system. The process may include providing a treatment configuration, such as a stent, balloon, ribbon, wire, or the like, coating at least a surface portion of the treatment configuration with a gold layer, and allowing a radiation-emitting self-assembled monolayer to form on the gold. A radiation emitting polymer layer can be allowed to form on the gold instead of the self-assembled monolayer.

The invention also includes a method for treating a patient at a treatment center with a radiation delivery system. The method includes determining the treatment configuration and type of radiation required for the patient; preparing a treatment configuration for the patient; covering at least a portion of the treatment configuration with gold; producing radionuclides at the treatment site; allowing a self-assembled monolayer to attach to the gold layer, the monolayer comprising a plurality of organic molecules, wherein each organic molecule has at least one sulfur-containing group, at least one chelating group capable of binding a radionuclide, and at least one radionuclide bound to said chelating group; attaching the radionuclides produced at the treatment center to the chelating group of the monolayer to produce the radiation delivery system; and using the radiation delivery system to deliver a therapeutic dose of radiation to a target tissue in the body.

BRIEF DESCRIPTION OF THE DRAWINGS

The accompanying drawings, which are incorporated in and form a part of the specification, illustrate the embodiment(s) of the present invention and, together with the description, serve to explain the principles of the invention. In the drawings.

DETAILED DESCRIPTION OF THE INVENTION

The present invention includes a radiation delivery system, referred to herein as a "locally labeled radiation delivery system" or LLRDS, which can be used for IVB to deliver a therapeutic dose of radiation to a lesion following PTCA. Although the description that follows relates to the use of the LLRDS for coronary IVB, it should be understood that the LLRDS could also be used for other medical applications for preventing or minimizing benign or malignant cellular proliferation, including interstitial brachytherapy (for treating prostate cancer, for example), intercavitary brachytherapy (for example for lung or gynecological cancer treatment applications), and interluminal/intravascular brachytherapy (peripheral blood vessel and arteriovenous shunt restenosis therapy and the like).

The LLRDS of the present invention includes a modified PTCA device with an attached radionuclide, preferably one with a short half-life and a high specific activity. The LLRDS of the present invention is "locally labeled," i.e. the radionuclide is attached to the system at, or near, the treatment center. Reference will now be made in detail to the present preferred embodiments of the invention, examples of which are illustrated in the accompanying drawings. Similar or identical structure is identified using identical callouts.

Figure 1:
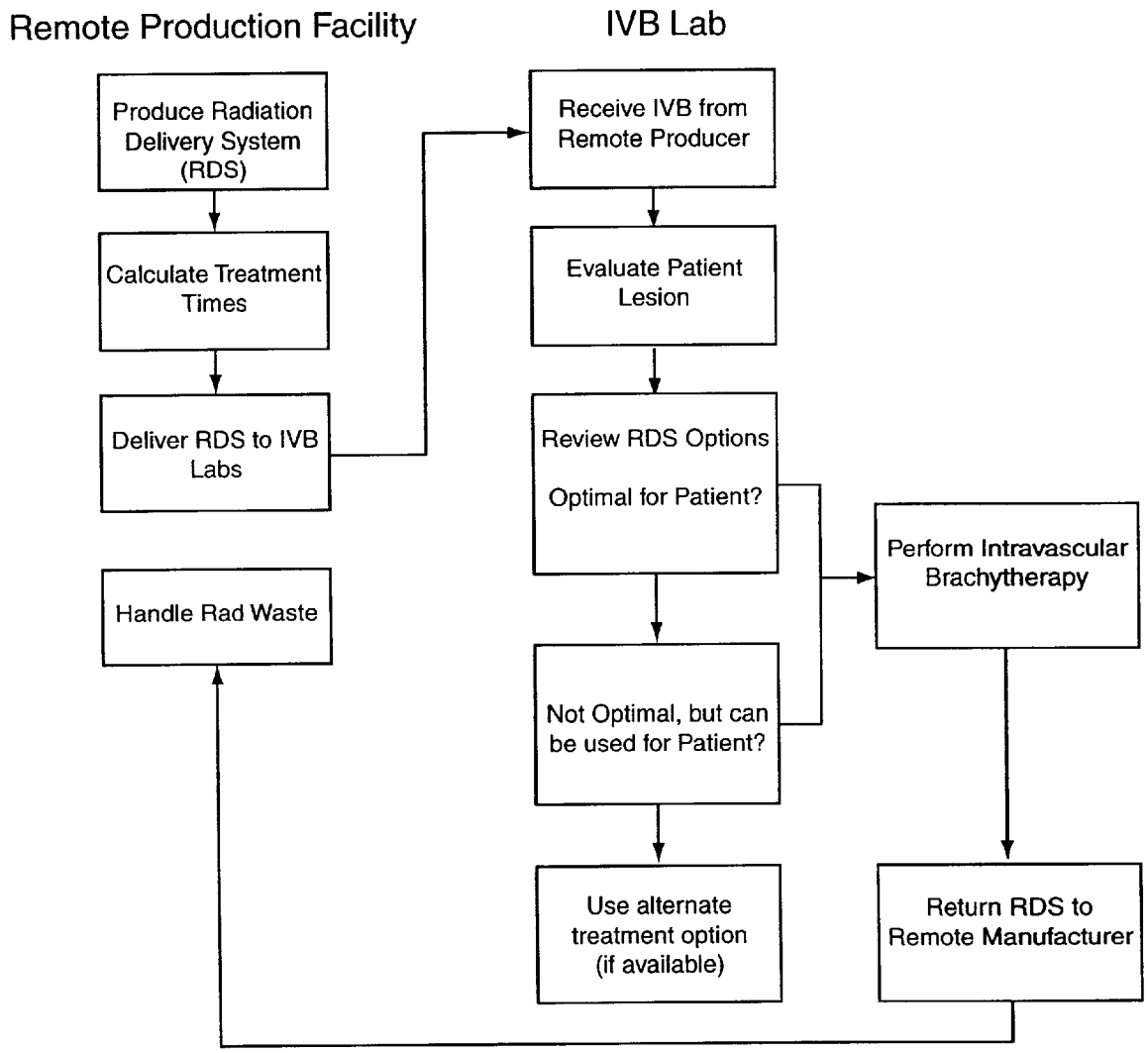
FIG. 1 shows a flow chart that summarizes the current IVB process.
Figure 2:
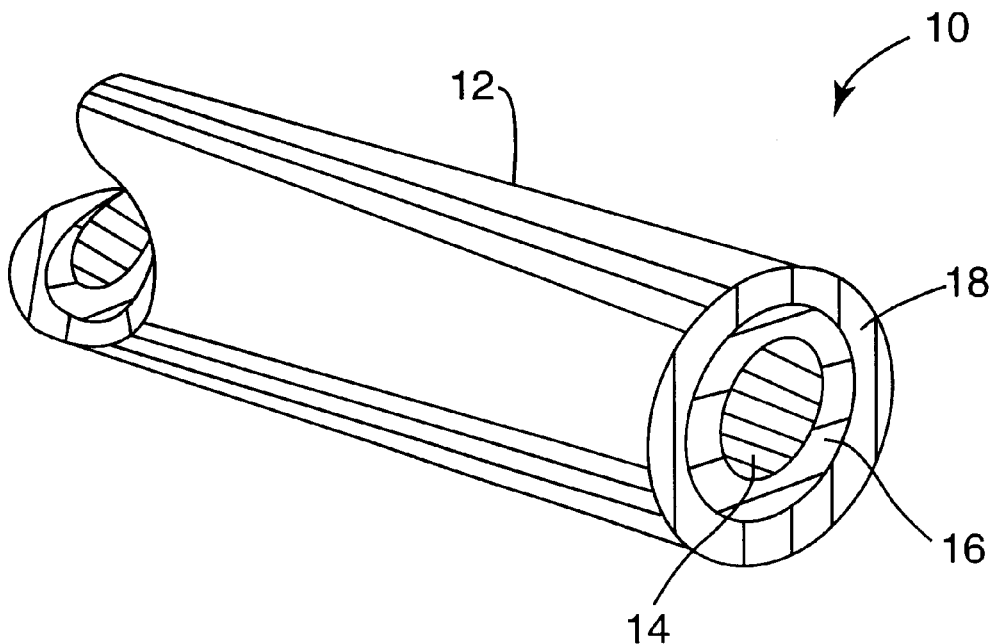
FIG. 2 shows a cross-sectional view of an embodiment of the present LLRDS invention.

An embodiment of the present LLRDS invention is shown in FIG. 2. Device 10 includes treatment configuration 12 having a body 14. A portion of body 14 is covered with a layer of metallic gold 16. Radiation-emitting layer 18 is a polymer layer or self-assembled monolayer of organic molecules, and has sulfur groups that bind it to gold layer 16. The polymer/SAM can include covalently bonded radionuclides, such as radioactive iodine in the form of iodide groups or radioactive phosphorus in the form of phosphate groups. The polymer/SAM can also include chelating groups that bind to the radionuclides. The LLRDS of the present invention is robust due to the oxidative stability of gold layer 16, the strong attraction between gold layer 16 and the SAM/polymer, the strong bonds bonds between the SAM/polymer and the attached radionuclides.

The gold layer can be produced using vapor deposition, electrochemical deposition, or by other known methods. Gold vapor deposition is preferred since it produces an Au(III) crystalline structure.

Figure 3:
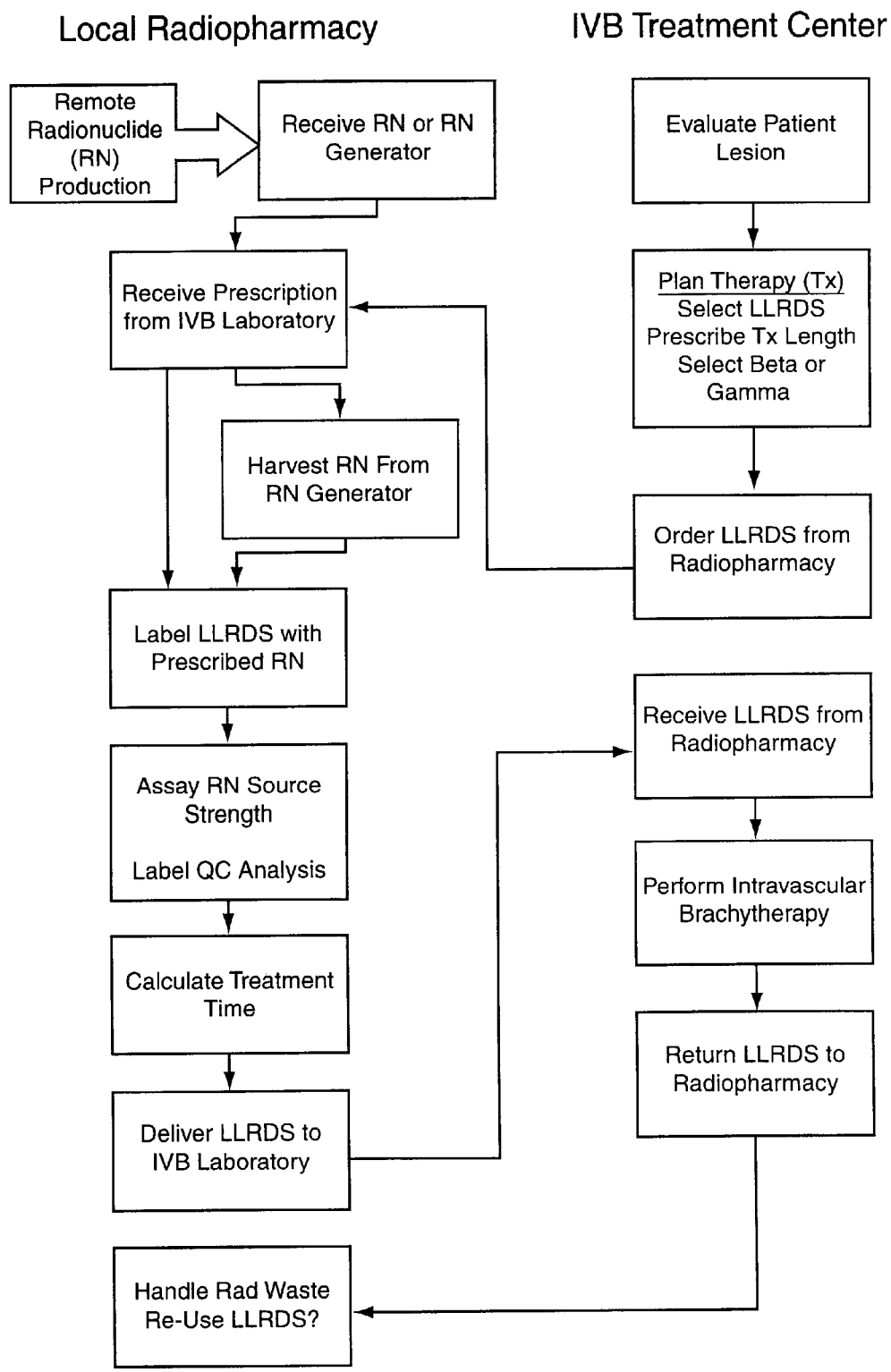
FIG. 3 shows a flow chart showing how the present LLRDS invention can be used.

FIG. 3 shows a flow diagram describing how the LLRDS is used. Briefly, the clinician prescribes a particular treatment configuration such as a stent, wire, ribbon, balloon catheter, or the like, and the type of radiation. The unlabeled treatment configuration is prepared, and then "locally labeled", i.e. coated with the radiation emitting layer just prior to treatment. This way, short-lived, high SA radionuclides that are optimal for IVB can be used. The LLRDS employs a tightly bound radionuclide, which minimizes loss of radionuclide and inadvertent or accidental contamination.

The LLRDS of the present invention can provide a range of therapeutic radiation dosages by adjusting the concentration of bound radionuclides. This could be accomplished by, for example, adjusting the thickness of the radiation-emitting layer. In the case of a radiation-emitting polymer layer, a thicker polymer layer, or one otherwise providing a higher concentration of radionuclides would provide a higher radiation dose over a chosen time period than a thinner layer or one with a lower concentration of radionuclides. The radionuclide concentration SA can be chosen so that a higher concentration of less active radionuclide or a lower concentration of a more active radionuclide could provide a similar dosage.

A wide variety of polymers can be used to provide radiation-emitting layer 18. These polymers, which all include sulfur groups that bind to the underlying gold layer, include polyethyleneimines, polyvinylamines, polyallylamines, polyamines, polyvinylalcohols, polyvinylpyrrolidines, and polyvinylpyridines. Examples of these types of polymers are described in U.S. Pat. No. 5,891,956 to B. E. Smith et al. entitled "Water-Soluble Polymers and Compositions Thereof", which is hereby incorporated by reference. The subset of polymers described in the '956 patent that contain sulfur groups (e.g. thiols, thioalkyls, thiolactams, and thioureas) and bind to radionuclides can be used with the present LLRDS invention. Those that do not bind effectively with radionuclides can be modified with additional chemical groups that do bind to radionuclides. Examples of polymers that can be used to provide the radiation-emitting layer include the following:

a polymer having the formula

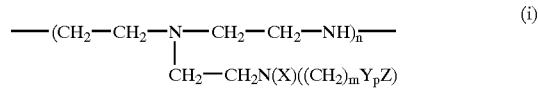

(i)

where X is a thiol, thioalkane, thiourea or thiolactam, where m is an integer selected from 0, 1, 2, 3, and 4, p is selected from 0 and 1, Y is selected from C=O, P=O, C=S, C(O)CH2C(O), and S, Z is selected from iodide, amine, alkylamine, arylamine, hydroxyl, oxyalkyl, oxyaryl, hydroxylamine, alkylhydroxylamine, arylhydroxylamine, dimethylpyrazolone, methylphenylpyrazolone, dimethylpyzarolone, oxycrown ethers, and azacrown ethers;

a polymer having the formula

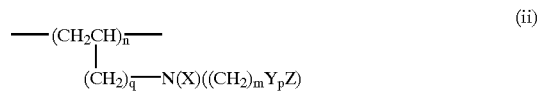

(ii)

where X is a thiol, thioalkane, thiourea, or thiolactam, where m is an integer selected from 0, 1, 2, 3, and 4, p is selected from 0 and 1, Y is selected from C=O, P=O, C=S, C(O)CH$_2$C(O), and S, Z is selected from iodide, amine, alkylamine, arylamine, hydroxyl, oxyalkyl, oxyaryl, hydroxylamine, alkylhydroxylamine, arylhydroxylamine, phosphate, dimethylpyrazolone, methylphenylpyrazolone, dimethylpyzarolone, oxycrown ethers, and azacrown ethers;

a polymer having the formula

(iii)

where X is a thiol, an thioalkane, thiourea, or thiolactam, where m is an integer selected from 0, 1, 2, 3, and 4, p is selected from 0 and 1, Y is selected from C=O, P=O, C=S, C(O)CH$_2$C(O), and S, Z is selected from iodide, amine, alkylamine, arylamine, hydroxyl, oxyalkyl, oxyaryl, hydroxylamine, alkylhydroxylamine, arylhydroxylamine, phosphate, dimethylpyrazolone, methylphenylpyrazolone, dimethylpyzarolone, oxycrown ethers, and azacrown ethers;

a polymer having the formula

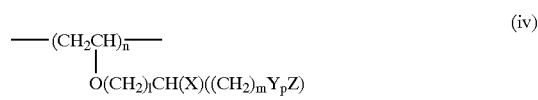

(iv)

where X is a thiol, a thioalkane, a thiourea, or thiolactam, where I is an integer selected from 0, 1, 2, 3, and 4, where m is an integer selected from 0, 1, 2, 3, and 4, p is selected from 0 and 1, Y is selected from C=O, P=O, C=S, C(O)CH$_2$C(O), and S, Z is selected from iodide, amine, alkylamine, arylamine, hydroxyl, oxyalkyl, oxyaryl, hydroxylamine, alkylhydroxylamine, arylhydroxylamine, phosphate, dimethylpyrazolone, methylphenylpyrazolone, dimethylpyzarolone, oxycrown ethers and azacrown ethers;

a polymer having the formula

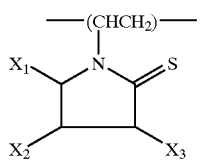 (v)

where X$_1$, X$_2$, and X$_3$ in each unit of the polymer is a group selected from H and

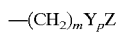
—(CH$_2$)$_m$Y$_p$Z where m is an integer selected from 0, 1, 2, 3, and 4, p is selected from 0 and 1, Y is selected from C=O, P=O, C=S, C(O)CH$_2$C(O), and S, Z is selected from iodide, amine, alkylamine, arylamine, hydroxyl, oxyalkyl, oxyaryl, hydroxylamine, alkylhydroxylamine, arylhydroxylamine, phosphate, dimethylpyrazolone, methylphenylpyrazolone, dimethylpyzarolone, oxycrown ethers and azacrown ethers; and a polymer having the formula

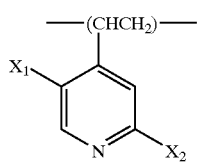 (vi)

where when X$_1$ is selected from H, thiol, thioalkane, thiolactam, thiourea, where X$_2$ is

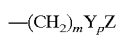
—(CH$_2$)$_m$Y$_p$Z where m is an integer selected from 0, 1, 2, 3, and 4, p is selected from 0 and 1, Y is selected from C=O, P=O, C=S, C(O)CH$_2$C(O), and S, Z is selected from iodide, amine, alkylamine, arylamine, hydroxyl, oxyalkyl, oxyaryl, hydroxylamine, alkylhydroxylamine, arylhydroxylamine, phosphate, dimethylpyrazolone, methylphenylpyrazolone, dimethylpyzarolone, oxycrown ethers and azacrown ethers;

where when X$_2$ is selected from thiol, alkylthiol, thiolactam, thiourea, X$_1$ is selected from

—(CH$_2$)$_m$Y$_p$Z where m is an integer selected from 0, 1, 2, 3, and 4, p is selected from 0 and 1, Y is selected from C=O, P=O, C=S, C(O)CH$_2$C(O), and S, Z is selected from iodide, amine, alkylamine, arylamine, hydroxyl, oxyalkyl, oxyaryl, hydroxylamine, alkylhydroxylamine, arylhydroxylamine, phosphate, dimethylpyrazolone, methylphenylpyrazolone, dimethylpyzarolone, oxycrown ethers and azacrown ethers.

The polymers could be water-soluble, but this is not necessary.

Examples of polyfunctional organic molecules that can be used to provide the SAM include thiols, thioalkanes, thioureas, thiolactams, and disulfides. For example, the SAM can be composed of the following types of molecules:

an organic molecule having the formula

Z(CH$_2$)$_n$X$_1$  (vii)

where n is an integer selected from 2, 3, 4, 5, 6, 7, 8, 9, 10, 11, 12, where Z is selected from thiols, thioalkane, thiolactam, and thiourea, and X is selected from iodide, amine, alkylamine, arylamine, hydroxyl, oxyalkyl, oxyaryl, hydroxylamine, alkylhydroxylamine, arylhydroxylamine, phosphate, carboxylate, dimethylpyrazolone, methylphenylpyrazolone, dimethylpyzarolone, oxycrown ethers and azacrown ethers, an organic molecule having the formula

Z(CH$_2$)$_n$X$_2$  (viii)

where n is an integer selected from 2, 3, 4, 5, 6, 7, 8, 9, 10, 11, and 12, Z is selected from thiols, alkylthianes, thioureas, and thiolactams, and X$_2$ is selected from iodide, amine, alkylamine, arylamine, hydroxyl, oxyalkyl, oxyaryl, hydroxylamine, alkylhydroxylamine, arylhydroxylamine, carboxylate, phosphate, dimethylpyrazolone, methylphenylpyrazolone, dimethylpyzarolone, oxycrown ethers and azacrown ethers;

an organic molecule having the formula

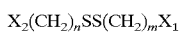
X$_2$(CH$_2$)$_n$SS(CH$_2$)$_m$X$_1$  (ix)

where n is an integer selected from 1, 2, 3, 4, 5, 6, 7, 8, 9, 10, 11, and 12, m is an integer selected from 1, 2, 3, 4, 5, 6, 7, 8, 9, 10, 11, and 12, and X$_1$ and X2x is selected independently from methyl, iodide, amine, alkylamine, arylamine, hydroxyl, oxyalkyl, oxyaryl, hydroxylamine, alkylhydroxylamine, arylhydroxylamine, carboxylate, phosphate, dimethylpyrazolone, methylphenylpyrazolone, dimethylpyzarolone, oxycrown ethers and azacrown ethers. These disulfides can be used to attentuate the dosage for a SAM. Coordination of the disulfide to the gold surface results in cleavage of the disulfide bond, and each sulfur binds to the gold. Therefore, by using a disulfide of the type shown above, only half of the species coordinated to the gold contains a radionuclide such as radioactive iodide or phosphorus, or can bind to a radioactive nuclide, such as an amine.

The term alkylamine is meant to include structures having an alkylamine group, and includes, for example, the following structures that are known to chelate with radionuclides such as $^{99m}$Tc:

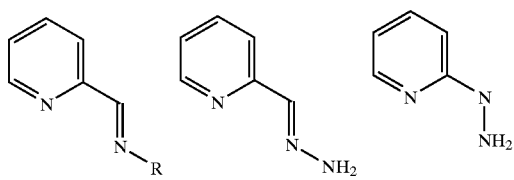

-continued

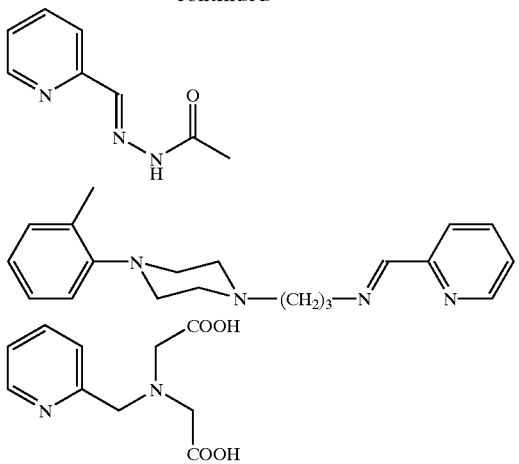

To form the SAM, the gold coated treatment configuration, i.e. stent, balloon, wire, ribbon, seed, or the like is immersed in a solution of the appropriate organic chelating ligand or mixture. Ligands having long alkyl chains are generally dissolved in organic solvents to insure solubility. Mixtures of chelating ligand and nonreactive adsorbate can be used to control the capacity of the SAM's per square unit area of bound radioisotope. Immersion times for the generation of the SAM will be on the order of minutes to hours depending on the material being chemisorbed onto the gold. Once the SAM is produced, the radionuclide is attached by immersion into a solution containing the radionuclide. The time required for radionuclide binding is dependent on the binding kinetics of the chelating group of the SAM and the particular radionuclide used. In the case of $^{99m}$Tc, such times should be short enough to ensure that the activity of the radioisotope has not decayed to levels below the therapeutic value.

It is important to note that the binding to a particular radionuclide can be affected by its oxidation state. This is particularly important for radionuclides that chelate to the SAM or polymer. While a radionuclide in one particular oxidation state, such as Tc(I) may bind strongly to a chelating amine, for example, the same radionuclide in a different oxidation state, such as Tc(VII) may bind weakly, or not at all. For effective combinations of radionuclide with SAM, the resulting radiation emitting layer produces a radiation dose that is extremely uniform across the lesion due to the uniformity and compactness of the SAM on the gold surface.

Variations in the surface area of the gold layer, the concentration of organic molecules on the gold layer, the chelating capacity a particular radionuclide, and the activity of the radionuclide are considered when producing the SAM for the LLRDS. The actual surface area, for example, of the gold coated portion of a guide wire is typically about 1.5–2 times greater than the theoretical surface area due to the unevenness of, and subtle variations in, the thickness of the surface.

A variety of beta-emitting and gamma-emitting radionuclides can be used with the LLRDS. Preferably, the radionuclide should be readily available to radiopharmacists, and easily and strongly attached to the radiation-emitting layer. Ideally, the radionuclide would have a high specific activity, and be produced at the treatment center such as a hospital or clinic, or nearby at, for example, a local commercial radiopharmacy to minimize loss of radioactivity during shipping. It should deliver a uniform dose at a high rate to the target region; irradiation of tissues outside the treatment zone should be minimal and variable densities due to, for example, the presence of calcified plaques, stents, etc. should not significantly affect the dose distribution.

The radionuclides listed in Table 2 were evaluated for use with an LLRDS. A wire treatment configuration centered within a 1.5-, 3.0-, or 4.5-mm blood vessel was selected to approximate a line source of radiation that provides a radiation dose at a prescription point located about 0.5 mm within the vessel wall of a target tissue. A plaque deposit was added to the blood vessel to provide a variable density aspect to the evaluation. The activity per unit source length required to deliver a specified dose rate at the prescription point, the mass per unit source length required to deliver a specified dose rate at the prescription point, the surface to prescription point dose ratio, which provides a measure of dose distribution uniformity, and the percent reduction of prescription point dose rate caused by the presence of plaque deposition inside vessel were considered in the evaluation. Each of these parameters was given equal weight for each vessel diameter. Based on these parameters, a relative ranking was obtained. Table 3 shows this ranking in order of most preferred to least preferred of widely available radionuclides, with most preferred at the top of each list.

TABLE 3

Relative Ranking of Radionuclides for LLRDS

| Beta Emitter | Gamma Emitter |
| --- | --- |
| $^{90}$Y | $^{111}$In |
| $^{188}$Re | $^{99m}$Tc |
| $^{32}$P | $^{67}$Ga |
| $^{91}$Y | $^{123}$I |
| $^{89}$Sr | $^{57}$Co |
| $^{210}$Bi | $^{169}$Yb |
| $^{131}$I | $^{201}$Tl |
| $^{186}$Re | $^{192}$Ir |

As Table 3 shows, $^{90}$Y, $^{188}$Re, $^{32}$P and $^{91}$Y are preferred beta emitting radionuclides and $^{111}$In, $^{99m}$Tc, $^{67}$Ga, and 1231I are preferred gamma radionuclides. The present LLRDS invention can also be used with other radionuclides.

Table 4 summarizes the half-life, type of radiation emitted, and energy yield for various radionuclides that are widely distributed to hospitals and commercial radiopharmacies (see M. P. Iturralde, "The Dictionary and Handbook of Nuclear Medicine and Clinical Imaging", CRC Press, Boca Raton, Fla.).

TABLE 4

Widely Distributed Radionuclides Suitable for LLRDS

| Radionuclide | Half-Life | Emission Type Energy (Yield) |
| --- | --- | --- |
| $^{67}$Ga | 78 h | Gamma |
|  |  | 93 keV (38%) |
|  |  | 185 keV (23%) |
|  |  | 300 keV (17%) |
| $^{111}$In | 67.4 h | Gamma |
|  |  | 171 keV (91%) |
|  |  | 247 keV (94%) |
| $^{123}$I | 13.3 h | Gamma |
|  |  | 159 keV (83%) |
| $^{32}$P | 14.3 d | Beta |
|  |  | 1709 keV (100%) |
| $^{89}$Sr | 52.7 d | Beta |
|  |  | 1463 keV (100%) |

Some of the preferred radionuclides can be produced using a generator system. Three generator systems are described in Table 5.

TABLE 5

Radionuclide Generator Systems

| Parent/Daughter | Half-Life | Daughter Emission Type Energy (Yield) |
|---|---|---|
| $^{90}$Sr/ | 29.5 y | Beta |
| $^{90}$Y | 2.7 d | 2.2 MeV (100%) |
| $^{99}$Mo/ | 66.7 h | Gamma |
| $^{99m}$Tc | 6.02 h | 140 keV (91%) |
| $^{188}$W/ | 69 d | Beta |
| $^{188}$Re | 16.9 h | 2.13 MeV |

The $^{99}$Mo/$^{99m}$Tc generator is currently used to generate $^{99m}$Tc for use in nuclear medicine laboratories present in most hospitals that perform PTCA.

Figure 4:
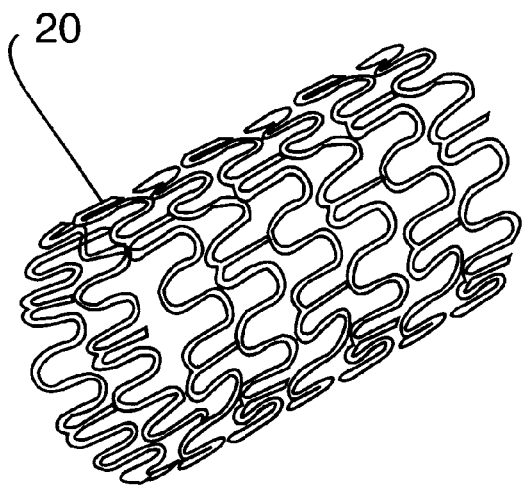
FIG. 4 shows a perspective view of a stent.
Figure 5A:
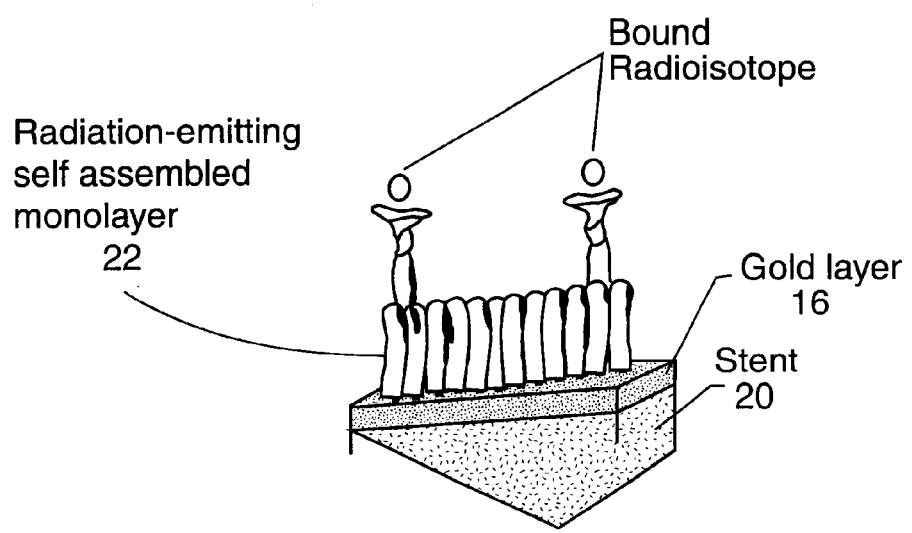
FIG. 5a shows a perspective view of a first embodiment of a stent LLRDS with an attached radiation-emitting self-assembled monolayer.
Figure 5B:
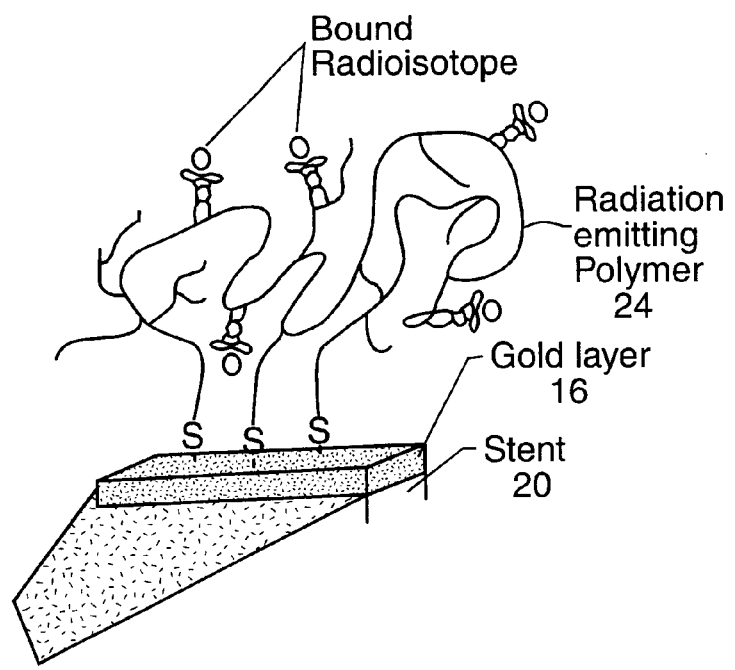
FIG. 5b shows a perspective view of a second embodiment of a stent LLRDS with an attached radiation-emitting polymer.

A wide variety of treatment configurations that include wires, ribbons, stents, balloons, and the like, can be used to provide an LLRDS. FIG. 4 shows a perspective view of a stent 20. FIG. 5a shows a perspective view of the surface of the stent 20, gold layer 16, and radiation emitting self assembled monolayer 22. FIG. 5b shows a perspective view of the stent 20, the attached gold layer 16, and radiation-emitting polymer 24 chemisorbed to the gold layer 16. Also shown are the chelating group of the polymer and the bound radionuclide.

Portions of the internal or external surface of a balloon can be coated with gold, after which the radiation-emitting layer, either a SAM or a polymer, can be chemisorbed to the gold. A balloon of this type can be incorporated into a fixed wire catheter, an over-the-wire catheter, a monorail catheter, or the like to provide an LLRDS of the present invention. Tables 6 and 7 summarize the radionuclide activity, required mass, and mass per unit area required for beta-emitting and gamma emitting radionuclides used with a balloon catheter having a profile of 0.56-mm, about the smallest profile for an over-the-wire balloon catheter currently used.

TABLE 6

Beta Emitter Concentrations for a 0.56-mm Profile Balloon

| Radionuclide | Radionuclide Activity (mCi) | Mass required ($\mu$g) | Mass per unit area of radionuclide ($\mu$g/mm$^2$) |
|---|---|---|---|
| $^{90}$Y | 27.7 | 0.0503 | 0.000954 |
| $^{188}$Re | 34.6 | 0.0347 | 0.000657 |
| $^{32}$P | 39.2 | 0.136 | 0.00258 |
| $^{91}$Y | 48.6 | 1.97 | 0.0373 |
| $^{89}$Sr | 51.7 | 1.84 | 0.0348 |
| $^{210}$Bi | 159.2 | 1.27 | 0.0240 |
| $^{131}$I | 2440.0 | 19.5 | 0.369 |
| $^{186}$Re | 264.0 | 1.38 | 0.0261 |

TABLE 7

Gamma emitter concentrations for a 0.56-mm profile balloon

| Radionuclide | Radionuclide Activity (mCi) | Mass required ($\mu$g) | Mass per unit area of radionuclide ($\mu$g/mm$^2$) |
|---|---|---|---|
| $^{99m}$Tc | 9440.0 | 1.77 | 0.0335 |
| $^{111}$In | 2504.0 | 5.91 | 0.112 |
| $^{123}$I | 5616.0 | 2.90 | 0.0550 |
| $^{67}$Ga | 5792.0 | 9.59 | 0.182 |
| $^{201}$Tl | 9840.0 | 45.6 | 0.864 |
| $^{57}$Co | 7520.0 | 880 | 16.7 |
| $^{169}$Yb | 3144.0 | 128 | 2.43 |

TABLE 7-continued

Gamma emitter concentrations for a 0.56-mm profile balloon

| Radionuclide | Radionuclide Activity (mCi) | Mass required ($\mu$g) | Mass per unit area of radionuclide ($\mu$g/mm$^2$) |
|---|---|---|---|
| $^{197}$Hg | 11920.0 | 47.5 | 0.900 |
| $^{192}$Ir | 1152.0 | 124 | 2.35 |

The mass (in micrograms) and surface concentration (in micrograms per square millimeter) can be estimated for a variety of radionuclides used to produce a wire type or ribbon type LLRDS. Tables 8 summarizes data estimated for variety of beta-emitting radionuclides used with a metallic wire LLRDS having a diameter of about 0.36 mm, and Table 9 for a nylon ribbon LLRDS having a diameter of about 0.76 mm. Each LLRDS would deliver a radiation dose of about 20 Gy for about 5 minutes to a target lesion about 20 millimeters long in a vessel having an inner diameter of about 3 mm wide.

TABLE 8

Target beta emitter data for 0.36-mm wires

| Radionuclide | Activity (mCi) | Mass ($\mu$g) | Area occupied by radionuclide ($\mu$g/mm$^2$) | Concentration ($\mu$g/mm$^3$) |
|---|---|---|---|---|
| $^{90}$Y | 27.7 | 0.0503 | 0.00148 | 0.0165 |
| $^{188}$Re | 34.6 | 0.0347 | 0.00102 | 0.0114 |
| $^{32}$P | 39.2 | 0.136 | 0.00401 | 0.0445 |
| $^{91}$Y | 48.6 | 1.97 | 0.0580 | 0.645 |
| $^{89}$Sr | 51.7 | 1.84 | 0.0541 | 0.601 |
| $^{210}$Bi | 159.2 | 1.27 | 0.0374 | 0.416 |
| $^{131}$I | 2440.0 | 19.5 | 0.574 | 6.38 |
| $^{186}$Re | 264.0 | 1.38 | 0.0406 | 0.451 |

TABLE 9

Target beta emitter data for 0.76-mm ribbons

| Radionuclide | Activity (mCi) | Mass ($\mu$g) | Area occupied by radionuclide ($\mu$g/mm$^2$) | Concentration ($\mu$g/mm$^3$) |
|---|---|---|---|---|
| $^{90}$Y | 27.7 | 0.0503 | 0.000703 | 0.00370 |
| $^{188}$Re | 34.6 | 0.0347 | 0.000484 | 0.00255 |
| $^{32}$P | 39.2 | 0.136 | 0.00190 | 0.00999 |
| $^{91}$Y | 48.6 | 1.97 | 0.0275 | 0.145 |
| $^{89}$Sr | 51.7 | 1.84 | 0.0256 | 0.135 |
| $^{210}$Bi | 159.2 | 1.27 | 0.0177 | 0.0932 |
| $^{131}$I | 2440.0 | 19.5 | 0.272 | 1.43 |
| $^{186}$Re | 264.0 | 1.38 | 0.0192 | 0.101 |

Tables 10 and 11 summarize data estimated for an LLRDS using a variety of gamma-emitting radionuclides with 0.36-mm wires and 0.76-mm ribbons, respectively.

TABLE 10

Target gamma emitter data for 0.36-mm wires

| Radionuclide | Activity (mCi) | Mass ($\mu$g) | Area occupied by radionuclide ($\mu$g/mm$^2$) | Concentration of radionuclide ($\mu$g/mm$^3$) |
|---|---|---|---|---|
| $^{99m}$Tc | 9440.0 | 1.77 | 0.0522 | 0.580 |
| $^{111}$In | 2504.0 | 5.91 | 0.174 | 1.94 |
| $^{123}$I | 5616.0 | 2.90 | 0.0855 | 0.950 |
| $^{67}$Ga | 5792.0 | 9.59 | 0.283 | 3.14 |

TABLE 10-continued

Target gamma emitter data for 0.36-mm wires

| Radionuclide | Activity (mCi) | Mass (μg) | Area occupied by radionuclide (μg/mm²) | Concentration of radionuclide (μg/mm³) |
|---|---|---|---|---|
| $^{201}$Tl | 9840.0 | 45.6 | 1.34 | 14.9 |
| $^{57}$Co | 7520.0 | 880 | 25.9 | 288 |
| $^{169}$Yb | 3144.0 | 128 | 3.77 | 41.9 |
| $^{197}$Hg | 11920.0 | 47.5 | 1.40 | 15.6 |
| $^{192}$Ir | 1152.0 | 124 | 3.66 | 40.6 |

TABLE 11

Target gamma emitter data for 0.76-mm ribbons

| Radionuclide | Activity (mCi) | Mass (μg) | Area occupied by Radionuclide (μg/mm²) | Concentration of radionuclide (μg/mm³) |
|---|---|---|---|---|
| $^{99m}$Tc | 9440.0 | 1.77 | 0.0247 | 0.130 |
| $^{111}$In | 2504.0 | 5.91 | 0.0825 | 0.434 |
| $^{123}$I | 5616.0 | 2.90 | 0.0405 | 0.213 |
| $^{67}$Ga | 5792.0 | 9.59 | 0.134 | 0.704 |
| $^{201}$Tl | 9840.0 | 45.6 | 0.636 | 3.35 |
| $^{57}$Co | 7520.0 | 880 | 12.3 | 64.7 |
| $^{169}$Yb | 3144.0 | 128 | 1.79 | 9.41 |
| $^{197}$Hg | 11920.0 | 47.5 | 0.663 | 3.49 |
| $^{192}$Ir | 1152.0 | 124 | 1.73 | 9.11 |

A source medium can be attached to a wire, ribbon, or the like, and a gold layer applied thereon. Source media, for example beads or seeds, can be attached to the distal end of a guidewire, layered with gold, and provided with a radiation emitting SAM/polymer. The vessel inner diameter limits the outer diameter of these systems. Tables 12 and 13 summarize data for beta- and gamma-emitting radionuclides, respectively, used with such a system having a diameter of about 1.2 mm, which is about in the middle range outer diameter for treatment catheters currently used.

TABLE 12

Target beta emitter concentrations for 1.2-mm diameter wires

| Radionuclide | Activity (mCi) | Mass (μg) | Area occupied by radionuclide (μg/mm²) | Concentration (μg/mm³) |
|---|---|---|---|---|
| $^{90}$Y | 27.7 | 0.0503 | 4.45E–04 | 1.48E–03 |
| $^{188}$Re | 34.6 | 0.0347 | 3.07E–04 | 1.02E–03 |
| $^{32}$P | 39.2 | 0.136 | 1.20E–03 | 4.01E–03 |
| $^{91}$Y | 48.6 | 1.97 | 1.74E–02 | 5.80E–02 |
| $^{89}$Sr | 51.7 | 1.84 | 1.62E–02 | 5.41E–02 |
| $^{210}$Bi | 159.2 | 1.27 | 1.12E–02 | 3.74E–02 |
| $^{131}$I | 2440.0 | 19.5 | 1.72E–01 | 5.74E–01 |
| $^{186}$Re | 264.0 | 1.38 | 1.22E–02 | 4.06E–02 |

TABLE 13

Target gamma emitter concentrations for 1.2-mm diameter wires

| Radionuclide | Activity (mCi) | Mass (μg) | Area occupied by Radionuclide (μg/mm²) | Concentration of radionuclide (μg/mm³) |
|---|---|---|---|---|
| $^{99m}$Tc | 9440.0 | 1.77 | 1.57E–02 | 5.22E–02 |
| $^{111}$In | 2504.0 | 5.91 | 5.22E–02 | 1.74E–01 |
| $^{123}$I | 5616.0 | 2.90 | 2.56E–02 | 8.55E–02 |
| $^{67}$Ga | 5792.0 | 9.59 | 8.48E–02 | 2.83E–01 |

TABLE 13-continued

Target gamma emitter concentrations for 1.2-mm diameter wires

| Radionuclide | Activity (mCi) | Mass (μg) | Area occupied by Radionuclide (μg/mm²) | Concentration of radionuclide (μg/mm³) |
|---|---|---|---|---|
| $^{201}$Tl | 9840.0 | 45.6 | 4.03E–01 | 1.34E+00 |
| $^{57}$Co | 7520.0 | 880 | 7.78E+00 | 2.59E+01 |
| $^{169}$Yb | 3144.0 | 128 | 1.13E+00 | 3.77E+00 |
| $^{197}$Hg | 11920.0 | 47.5 | 4.20E–01 | 1.40E+00 |
| $^{192}$Ir | 1152.0 | 124 | 1.10E+00 | 3.66E+00 |

Low-dose-rate (LDR) brachytherapy procedures that are effective in cancer treatment involve delivering the dose over a period of several days. In contrast, currently used, permanently implanted radiation delivery systems deliver a radiation dose over a period of weeks ($^{32}$P systems) or months (125I systems). Ideally, the radionuclide used in a stent-based LLRDS will have 95% of its dose delivered within the typical LDR brachytherapy time frame (up to 72 hours). This approach will allow usage of gamma emitting radionuclides that were previously excluded because of radiation safety reasons. It is impractical to allow a patient to be a radiation hazard to others for a long period of time. Preferred embodiments of the present LLRDS invention employ radionuclides that can deliver 95% of the radiation dose within 72 hours, such as beta emitter $^{188}$Re and gamma emitters $^{99m}$Tc and 123I.

Table 14 summarizes data calculated for a stent LLRDS that delivers a treatment dose of 20 Gy to a target lesion about 20 mm long in a vessel with an inner diameter of 3-mm. About 10% of the area of the vessel is in contact with the stent.

TABLE 14

Target radionuclide concentrations for 3 mm LLRDS Stent

| Radionuclide | Radiation | Activity (mCi) | Mass (μg) | Concentration (μg/mm²) | Patient release time |
|---|---|---|---|---|---|
| $^{188}$Re | Beta | 0.12 | 1.25E–04 | 4.42E–06 | Immediate. |
| $^{99m}$Tc | Gamma | 90.9 | 1.70E–02 | 6.03E–04 | 9.6 hr |

The table indicates that target radionuclide labeling concentrations using stent-based LLRDS technologies are very low. Use of such a system would require less radioactive material and subsequently reduce radiation safety concerns. Government regulations currently place restrictions on patients that have greater than 30 mCi of radioactive material in their bodies. Patients could be released from care immediately after using $^{188}$Re and 123I, while treatment with $^{99m}$Tc would only require a 10-hour hospital stay, if any at all. 123I and $^{99m}$Tc may be especially advantageous since gamma-emitters have not shown the "candy wrapper" effects seen with beta emitters. In addition, the identified radionucliides are currently widely available in radiopharmacies, and their strength can be easily assayed using dose calibrators present in nuclear medicine laboratories.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A radiation delivery system, comprising:
   (a) a treatment configuration having a surface;
   (b) a gold layer metal attached to at least a portion of said surface of said treatment configuration;
   (c) a radiation emitting self-assembled monolayer chemisorbed to said gold metal layer.

2. The radiation delivery system of claim 1, wherein said treatment configuration comprises stents, wires, ribbons, and balloon catheters.

3. The radiation delivery system of claim 1, wherein said radiation emitting self assembled monolayer comprises a plurality of organic molecules, wherein each organic molecule includes at least one sulfur containing group and at least one covalently bonded radionuclide.

4. The radiation delivery system of claim 1, wherein said radiation-emitting self assembled monolayer comprises a plurality of organic molecules, wherein each organic molecule has at least one sulfur-containing group, at least one chelating group capable of binding a radionuclide, and at least one radionuclide bound to said chelating group.

5. The radiation delivery system of claim 3, wherein said organic molecules have the formula $$Z(CH_2)_n X_1 \qquad (i)$$

where n is an integer selected from 2, 3, 4, 5, 6, 7, 8, 9, 10, 11, 12, where Z is selected from thiol, thioalkane, thiolactam, and thiourea, and $X_1$ is selected from iodide, amine, alkylamine, arylamine, hydroxyl, oxyalkyl, axyaryl, hydroxylamine, alkylhydroxylamine, arylhydroxylamine, phosphate, carboxylate, dimethylpyrazolone, methylphenylpyrazolone, dimethylpyzarolone, oxycrown ethers and azacrown ethers;

$$Z(CH_2)_n X_2 \qquad (ii)$$

where n is an integer selected from 2, 3, 4, 5, 6, 7, 8, 9, 10, 11, and 12, Z is selected from thiol, thioalkane, thiourea, and thiolactam, and $X_2$ is selected from iodide, amine, alkylamine, arylamine, hydroxyl, oxyalkyl, axyaryl, hydroxylamine, alkylhydroxylamine, arylhydroxylamine, carboxylate, phosphate, dimethylpyrazolone, methylphenylpyrazolone, dimethylpyzarolone, oxycrown ethers and azacrown ethers;

$$X_4(CH_2)_n SS(CH_2)_m X_3 \qquad (iii)$$

where n is an integer selected from 1, 2, 3, 4, 5, 6, 7, 8, 9, 10, 11, and 12, m is an integer selected from 1, 2, 3, 4, 5, 6, 7, 8, 9, 10, 11, and 12, and $X_3$ and $X_4$ are selected independently from methyl, iodide, amine, alkylamine, arylamine, hydroxyl, oxyalkyl, axyaryl, hydroxylamine, alkylhydroxylamine, arylhydroxylamine, carboxylate, phosphate, dimethylpyrazolone, methylphenylpyrazolone, dimethylpyzarolone, oxycrown ethers and azacrown ethers.

6. The radiation delivery system of claim 4, wherein said organic molecules have the formula $$Z(CH_2)_n X_1 \qquad (i)$$

where n is an integer selected from 2, 3, 4, 5, 6, 7, 8, 9, 10, 11, 12, where Z is selected from thiol, thioalkane, thiolactam, and thiourea, and $X_1$ is selected from iodide, amine, alkylamine, arylamine, hydroxyl, oxyalkyl, axyaryl, hydroxylamine, alkylhydroxylamine, arylhydroxylamine, phosphate, carboxylate, dimethylpyrazolone, methylphenylpyrazolone, dimethylpyzarolone, oxycrown ethers and azacrown ethers;

$$Z(CH_2)_n X_2 \qquad (ii)$$

where n is an integer selected from 2, 3, 4, 5, 6, 7, 8, 9, 10, 11, and 12, Z is selected from thiol, thioalkane, thiourea, and thiolactam, and $X_2$ is selected from iodide, amine, alkylamine, arylamine, hydroxyl, oxyalkyl, axyaryl, hydroxylamine, alkylhydroxylamine, arylhydroxylamine, carboxylate, phosphate, dimethylpyrazolone, methylphenylpyrazolone, dimethylpyzarolone, oxycrown ethers and azacrown ethers;

$$X_4(CH_2)_n SS(CH_2)_m X_3 \qquad (iii)$$

where n is an integer selected from 1, 2, 3, 4, 5, 6, 7, 8, 9, 10, 11, and 12, m is an integer selected from 1, 2, 3, 4, 5, 6, 7, 8, 9, 10, 11, and 12, and $X_3$ and $X_4$ are selected independently from methyl, iodide, amine, alkylamine, arylamine, hydroxyl, oxyalkyl, axyaryl, hydroxylamine, alkylhydroxylamine, arylhydroxylamine, carboxylate, phosphate, dimethylpyrazolone, methylphenylpyrazolone, dimethylpyzarolone, oxycrown ethers and azacrown ethers.

7. The radiation delivery system of claim 3, wherein said radionuclide is selected from the group consisting of $^{90}Y$, $^{188}Re$, $^{32}P$, $^{91}Y$, $^{89}Sr$, $^{210}Bi$, $^{131}I$, $^{186}Re$, $^{111}In$, $^{99m}Tc$, $^{67}Ga$, $123I$, $^{57}Co$, $^{169}Yb$, $^{201}Tl$, and $^{192}Ir$.

8. The radiation delivery system of claim 4, wherein said radionuclide is selected from the group consisting of $^{90}Y$, $^{188}Re$, $^{32}P$, $^{91}Y$, $^{89}Sr$, $^{210}Bi$, $^{131}I$, $^{186}Re$, $^{111}In$, $^{99m}Tc$, $^{67}Ga$, $^{123}I$, $^{57}Co$, $^{169}Yd$, $^{201}Tl$, and $^{192}Ir$.

9. A radiation delivery system, comprising:
   (a) a treatment configuration having a surface;
   (b) a gold layer attached to at least a portion of said surface of said treatment configuration; and
   (c) a radiation-emitting polymer layer comprising an organic polymer having attached radionuclides, said radiation emitting polymer being chemisorbed to said gold layer.

10. The radiation delivery system of claim 9, wherein said treatment configuration comprises stents, wires, ribbons, and balloon catheters.

11. The radiation delivery system of claim 9, wherein said radiation emitting polymer comprises an organic polymer backbone, sulfur containing groups attached to the polymer for binding the polymer to the gold layer, and radionuclides covalently bonded to the polymer.

12. The radiation delivery system of claim 9, wherein said radiation-emitting polymer layer comprises an organic polymer backbone, sulfur containing groups attached to the polymer for binding the polymer to the gold layer, and radionuclides that are chelated to the polymer.

13. The radiation delivery system of claim 9, wherein said organic polymer comprises a polymer having the formula $$—(CH_2—CH_2—N—CH_2—CH_2—NH)_n— \atop {\phantom{xxxxx}|\phantom{xxxxxxxxxxxxxxxx}} \atop CH_2—CH_2N(X)((CH_2)_m Y_p Z) \qquad (i)$$

where X is selected from thiol, thioalkane, thiourea, and thiolactam, where m is an integer selected from 0, 1, 2, 3, and 4, p is selected from 0 and 1, Y is selected from C=O, P=O, C=S, C(O)CH$_2$C(O), and S, Z is selected from iodide, amine, alkylamine, arylamine, hydroxyl, oxyalkyl, axyaryl, hydroxylamine, alkylhydroxylamine, arylhydroxylamine, dimethylpyrazolone, methylphenylpyrazolone, dimethylpyzarolone, oxycrown ethers, and azacrown ethers;

a polymer having the formula

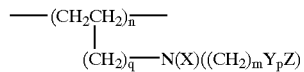
(ii)

where X is selected from thiol, thioalkane, thiourea, and thiolactam, where m is an integer selected from 0, 1, 2, 3, and 4, p is selected from 0 and 1, Y is selected from C=O, P=O, C=S, C(O)CH$_2$C(O), and S, Z is selected from iodide, amine, alkylamine, arylamine, hydroxyl, oxyalkyl, axyaryl, hydroxylamine, alkylhydroxylamine, arylhydroxylamine, phosphate, dimethylpyrazolone, methylphenylpyrazolone, dimethylpyzarolone, oxycrown ethers, and azacrown ethers;

a polymer having the formula

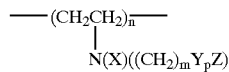
(iii)

where X is selected from thiol, thioalkane, thiourea, and thiolactam, where m is an integer selected from 0, 1, 2, 3, and 4, p is selected from 0 and 1, Y is selected from C=O, P=O, C=S, C(O)CH$_2$C(O), and S, Z is selected from iodide, amine, alkylamine, arylamine, hydroxyl, oxyalkyl, axyaryl, hydroxylamine, alkylhydroxylamine, arylhydroxylamine, phosphate, dimethylpyrazolone, methylphenylpyrazolone, dimethylpyzarolone, oxycrown ethers, and azacrown ethers;

a polymer having the formula

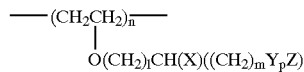
(iv)

where X is selected from thiol, thioalkane, thiourea, and thiolactam, where I is an integer selected from 0, 1, 2, 3, and 4, where m is an integer selected from 0, 1, 2, 3, and 4, where p is selected from 0 and 1, Y is selected from C=O, P=O, C=S, C(O)CH$_2$C(O), and S, Z is selected from iodide, amine, alkylamine, arylamine, hydroxyl, oxyalkyl, axyaryl, hydroxylamine, alkylhydroxylamine, arylhydroxylamine, phosphate, dimethylpyrazolone, methylphenylpyrazolone, dimethylpyzarolone, oxycrown ethers and azacrown ethers;

a polymer having the formula

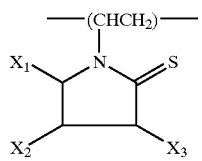
(v)

where $X_1$, $X_2$, and $X_3$ in each unit of the polymer is a group selected from H and

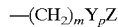

where m is an integer selected from 0, 1, 2, 3, and 4, p is selected from 0 and 1, Y is selected from C=O, P=O, C=S, C(O)CH$_2$C(O), and S, Z is selected from iodide, amine, alkylamine, arylamine, hydroxyl, oxyalkyl, axyaryl, hydroxylamine, alkylhydroxylamine, arylhydroxylamine, phosphate, dimethylpyrazolone, methylphenylpyrazolone, dimethylpyzarolone, oxycrown ethers and azacrown ethers; and a polymer having the formula

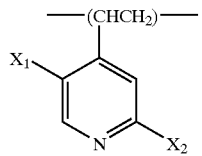
(vi)

where when $X_1$ is selected from H, thiol, alkylthiol, thiolactam, thiourea, $X_2$ is

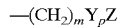

where m is an integer selected from 0, 1, 2, 3, and 4, p is selected from 0 and 1, Y is selected from C=O, P=O, C=S, C(O)CH$_2$C(O), and S, Z is selected from iodide, amine, alkylamine, arylamine, hydroxyl, oxyalkyl, axyaryl, hydroxylamine, alkylhydroxylamine, arylhydroxylamine, phosphate, dimethylpyrazolone, methylphenylpyrazolone, dimethylpyzarolone, oxycrown ethers and azacrown ethers;

where when $X_2$ is selected from thiol, alkylthiol, thiolactam, thiourea, $X_1$ is selected from

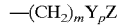

where m is an integer selected from 0, 1, 2, 3, and 4, p is selected from 0 and 1, Y is selected from C=O, P=O, C=S, C(O)CH$_2$C(O), and S, Z is selected from iodide, amine, alkylamine, arylamine, hydroxyl, oxyalkyl, axyaryl, hydroxylamine, alkylhydroxylamine, arylhydroxylamine, phosphate, dimethylpyrazolone, methylphenylpyrazolone, dimethylpyzarolone, oxycrown ethers and azacrown ethers.

14. The radiation delivery system of claim 11, wherein said radionuclide is selected from the group consisting of $^{90}$Y, $^{188}$Re, $^{32}$P, $^{91}$Y, $^{89}$Sr, $^{210}$Bi, 131I, $^{186}$Re, $^{111}$In, $^{99m}$Tc, $^{67}$Ga, 123I, $^{57}$Co, $^{169}$Yb, $^{201}$Tl, and $^{192}$Ir.

15. The radiation delivery system of claim 12, wherein said radionuclide is selected from the group consisting of $^{90}$Y, $^{188}$Re, $^{32}$P, $^{91}$Y, $^{89}$Sr, $^{210}$Bi, 131I, $^{186}$Re, $^{111}$In, $^{99m}$Tc, $^{67}$Ga, 123I, $^{57}$Co, $^{169}$Yb, $^{201}$Tl, and $^{192}$Ir.

* * * * *